US011348702B2

(12) United States Patent
O'Hara

(10) Patent No.: US 11,348,702 B2
(45) Date of Patent: May 31, 2022

(54) SYSTEM, EMANATION GENERATOR, AND PROCESS FOR PRODUCTION OF HIGH-PURITY THERAPEUTIC RADIOISOTOPES

(71) Applicant: BATTELLE MEMORIAL INSTITUTE, Richland, WA (US)

(72) Inventor: Matthew J. O'Hara, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 15/675,529

(22) Filed: Aug. 11, 2017

(65) Prior Publication Data

US 2018/0047474 A1 Feb. 15, 2018

Related U.S. Application Data

(60) Provisional application No. 62/373,661, filed on Aug. 11, 2016.

(51) Int. Cl.
| | |
|---|---|
| *A61K 9/00* | (2006.01) |
| *G21G 4/08* | (2006.01) |
| *B01J 20/06* | (2006.01) |
| *C01B 23/00* | (2006.01) |
| *C01G 21/00* | (2006.01) |
| *A61K 51/00* | (2006.01) |
| *G21G 4/10* | (2006.01) |
| *G21G 1/00* | (2006.01) |
| *A61K 51/12* | (2006.01) |

(52) U.S. Cl.
CPC ............... *G21G 4/08* (2013.01); *A61K 51/00* (2013.01); *A61K 51/1289* (2013.01); *B01J 20/06* (2013.01); *C01B 23/0073* (2013.01); *C01G 21/00* (2013.01); *G21G 1/0005* (2013.01); *G21G 4/10* (2013.01); *G21G 2001/0084* (2013.01); *G21G 2001/0094* (2013.01)

(58) Field of Classification Search
CPC ........................................................ G21G 4/08
See application file for complete search history.

(56) References Cited

U.S. PATENT DOCUMENTS

| | | | | |
|---|---|---|---|---|
| 2009/0162278 | A1* | 6/2009 | Ravn ....................... | G21G 1/001 424/1.37 |
| 2014/0186268 | A1* | 7/2014 | Vasiljeva ............... | A61K 33/26 424/9.321 |

* cited by examiner

*Primary Examiner* — Paul W Dickinson
(74) *Attorney, Agent, or Firm* — Wells St. John P.S.

(57) ABSTRACT

An isotope production system, emanation generator, and process are disclosed for production of high-purity radioisotopes. In one implementation example, high-purity Pb-212 and/or Bi-212 isotopes are produced suitable for therapeutic applications. In one embodiment the process includes transporting gaseous radon-220 from a radium-224 bearing generator which provides gas-phase separation of the Rn-220 from the Ra-224 in the generator. Subsequent decay of the captured Rn-220 accumulates high-purity Pb-212 and/or Bi-212 isotopes suitable for direct therapeutic applications. Other high-purity product isotopes may also be prepared.

13 Claims, 8 Drawing Sheets

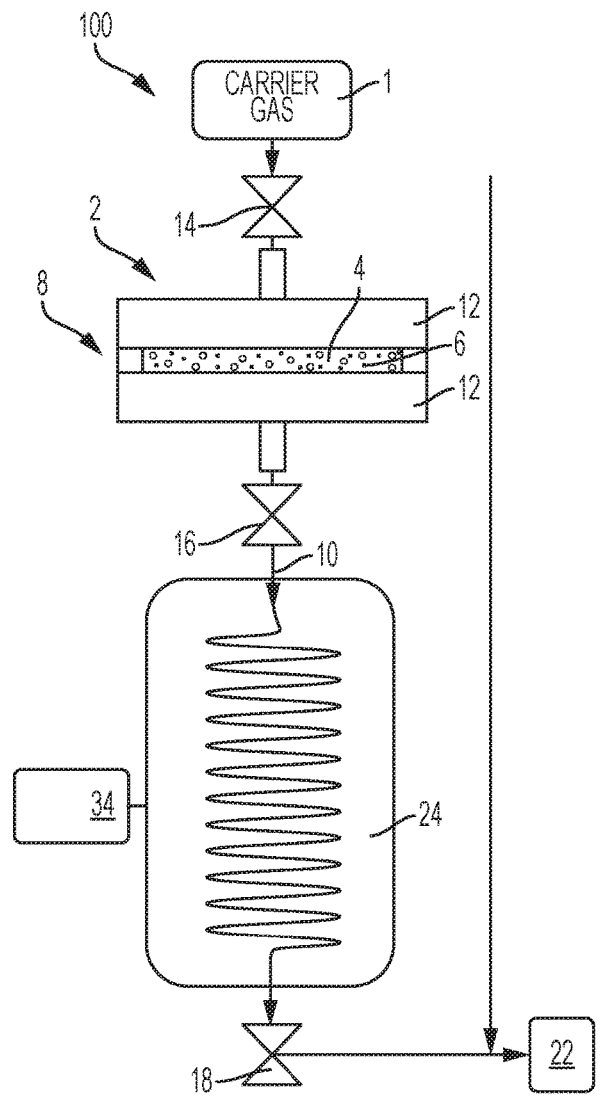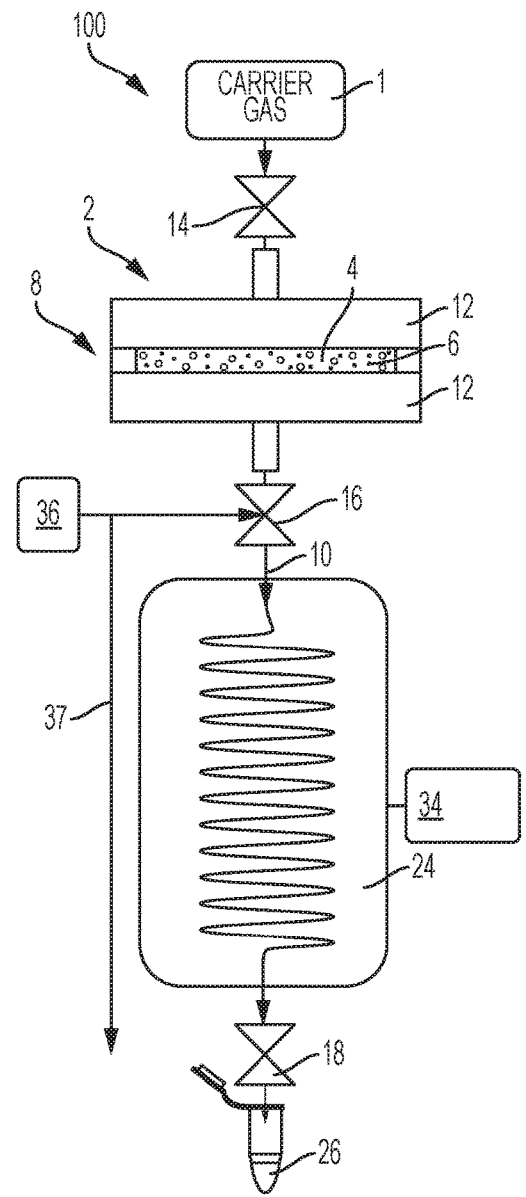
FIG. 1A
FIG. 1B

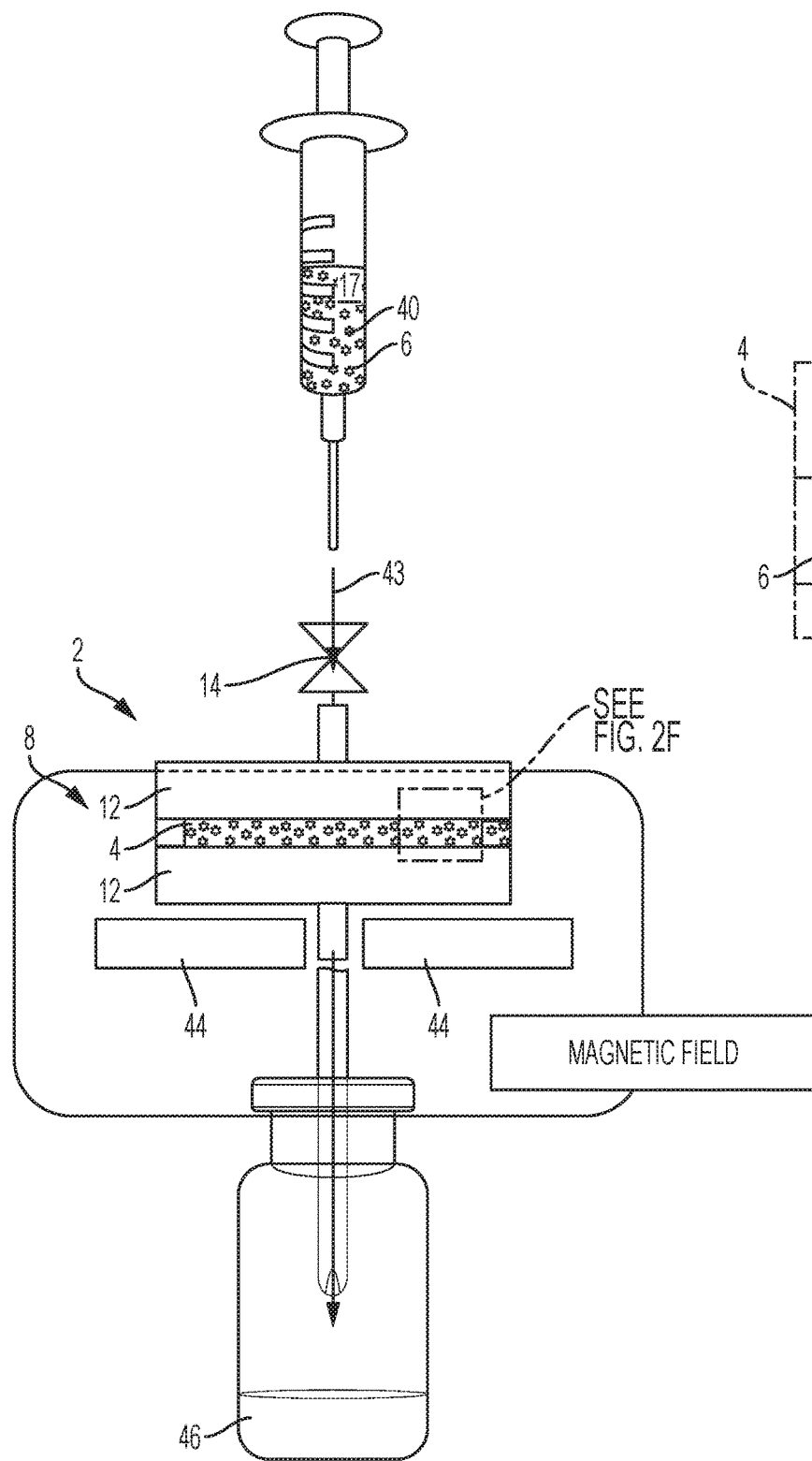
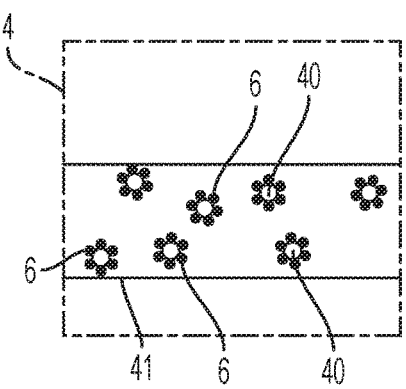
FIG. 2F
FIG. 2E

SYSTEM, EMANATION GENERATOR, AND PROCESS FOR PRODUCTION OF HIGH-PURITY THERAPEUTIC RADIOISOTOPES

CROSS REFERENCE TO RELATED APPLICATIONS

This is a non-provisional application that claims priority from U.S. Provisional Patent Application No. 62/373,661 filed 11 Aug. 2016 entitled "Gas Emanation System, Generator, and Process for Production of High-Purity Radioisotopes" which is incorporated in its entirety by reference herein.

STATEMENT REGARDING RIGHTS TO INVENTION MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

FIELD OF THE INVENTION

This disclosure relates to production of high purity radionuclides.

BACKGROUND OF THE INVENTION

The alpha emitting radionuclide bismuth-212 (Bi-212) [half-life=60.6 min.], a daughter product of lead-212 (Pb-212) [half-life=10.6 hrs.], is a promising radionuclide for use in targeted alpha therapy. Pb-212 can be used as an in vivo generator of Bi-212 giving labeled antibodies time to locate and bind to cancer cells while the Bi-212 isotope is generated thus facilitating a longer therapy. Bi-212 can also be utilized as a therapeutic isotope independent of its Pb-212 parent. An added advantage of the Pb-212 and/or Bi-212 isotopes is the relatively abundant sources of natural thorium-232 (Th-232) and legacy sources such as thorium-228 (Th-228) and uranium-232 (U-232) that can provide alpha isotopes for current and future therapy needs. Current generators for producing Pb-212 and/or Bi-212 isotopes are column-based generators that employ source isotopes such as Th-228 and/or radium-224 (Ra-224) (the immediate decay daughter of Th-228) that are adsorbed onto a cation exchange resin in an exchange column from which the Pb-212 and/or Bi-212 isotopes are recovered from the resin. However, while generators that employ a Th-228 source isotope (half-life=1.9 yrs) can provide a long-term supply of Pb-212 and Bi-212 isotopes, these generators have well-known problems. First, Th-228 generators are high-activity generators that can cause radiolytic failure in the generator columns over time and release high energy contaminates into the Pb-212 and/or Bi-212 solutions recovered from these columns that can deliver deleterious radiation doses. Th-228 generators in the prior art also experience characteristic decreases in radon yields over time due to radiolytic breakdown of organic capture materials such as barium-stearate utilized to contain the isotope sources. Severe contamination can also result if a breach in the generator column takes place due to prolonged radiolysis by the high energy source isotopes therein. Generators that employ Ra-224 as a source isotope are considered a generally safer source of Pb-212 and Bi-212 isotopes compared to Th-228 generators given their considerably shorter half-life (3.6 days). The U.S. Department of Energy's National Isotope Development Center (NIDC) supplies Ra-224 generators in which the Ra-224 source isotopes are separated and purified from a Th-228 and/or U-232 stock solution and again adsorbed onto a cation exchange resin in an exchange column. Daughter products Pb-212 and/or Bi-212 generated from the decay of Ra-224 and Rn-220 are periodically eluted from the column using acidic solutions such as hydrochloric or hydriodic acid or mixtures of these acids. However, exchange resins utilized in these generators are also prone to radiolytic breakdown that can result in breakthrough of Ra-224 isotopes from the generator column that contaminate solutions containing the recovered Pb-212 and/or Bi-212 isotopes. This again can result in unnecessary or unacceptable radiation doses to the patient. Additionally, these generators can demonstrate low Pb-212 and/or Bi-212 yields due to gaseous diffusion of the intermediate noble gas daughter Rn-220 deep into the exchange resin beads in-situ. Accordingly, new generator sources and processes are needed for production of high-purity therapeutic radioisotopes and other similar isotopes.

SUMMARY

This disclosure details an isotope production system, emanation generator, and process for production of high purity isotopes including those utilized for therapeutic applications. The isotope production system, emanation generator, and process address various problems in prior art isotope production systems including eliminating radiolytic degradation and breakthrough of high energy isotopes such as Ra-224 and Th-228 that can contaminate recovered isotopes; and eliminating reduction in isotope yields in prior art generators caused by radiolytic breakdown of organic capture materials and diffusion of radon gas into organic capture materials. In one embodiment, the emanation system includes an emanation device or generator having an emanation source loaded with a source isotope that generates a radioactive gas that is released and emanated from the emanation source device which separates the emanated radioactive gas from the source isotope as a pure radioactive gas product and a collection device or system that collects the radioactive gas and retains the gas for a time sufficient to decay and from one or more high purity radioactive daughter isotopes therein. The source isotope can include thorium isotopes, radium isotopes, and combinations of thorium and radium isotopes. Exemplary source isotopes include Thorium-228 (Th-228) and/or Radium-224 (Ra-224); Thorium-227 (Th-227) and/or Radium-223 (Ra-223); or Thorium-230 (Th-230) and/or Radium-226 (Ra-226) and combinations thereof. The source isotope can be sorbed or deposited onto particle surfaces or a permeable support such as a gas-permeable support and utilized in the emanation source. The source isotope can also be sorbed or deposited onto magnetic or paramagnetic metal oxide particles and utilized in the emanation source. Various methods can be utilized to sorb or deposit the source isotopes onto the support in the emanation source such as by electrolytic deposition or by introduction of source isotopes and/or particles in fluids and particle suspensions, for example. Radioactive gaseous daughter or granddaughter isotopes generated by the source isotopes in the emanation source can include radon (Rn) isotopes such as Rn-219; Rn-220; Rn-222, and radioactive noble gases such as radioactive xenon isotopes and radioactive krypton isotopes. The radioactive gas is transported out of the emanation source out of the emanation generator separating the radioactive gas from the source isotope. The radioactive gas can be captured and collected by a collection device and retained for a time sufficient to allow decay of the radioactive gas to yield one or more high-purity daughter isotopes. Radioactive daughter isotopes depend on the source isotopes that are utilized. Radioactive daughter isotopes can include Pb-212, Bi-212, Pb-211, Bi-211, Pb-214, Bi-214, and combinations of these daughter isotopes. Daughter isotopes can also comprise radioactive xenon isotopes, radioactive krypton isotopes or other radioactive noble gases. These daughter isotopes can be utilized, for example, as therapeutic isotopes in radiotherapeutic applications. The collection device can include a cooling device configured to cool the radioactive gas emanated from the emanation device. The collection device can also include a cryogen such as liquid nitrogen or dry ice bath. The collection device can also include a capture material or sorbent comprised of a soluble salt configured to sorb the radioactive gas emanated from the emanation device therein. The soluble salt may be introduced as a thin film or a packed salt. Soluble salts can include soluble organic salts such as urea; soluble inorganic salts including buffer salts such as acetate buffer salts, carbonate/HEPES buffer salts, and physiological saline, or other soluble capture materials. In some embodiments, the capture material can be a thin film comprised of a lipophilic liquid such as a long-chain hydrocarbon included dodecane, for example, that extracts the radioactive gas emanated from the emanation device therein. Alternatively, in some embodiments, the capture material can be a lipophilic liquid coated onto solid supports such as metal or resin beads. The collection device can also utilize a combination of cooling or cryogenic temperatures along with various capture materials described herein. The system can also include an eluent delivery device or system configured to deliver fluids through the collection device to recover the radioactive daughter isotopes such as biologically compatible aqueous solutions, for example. Radioactive daughter isotopes include Pb-212 and/or Bi-212; Pb-211 and/or Bi-211; and Pb-214 and/or Bi-214 including daughter isotopes thereof.

In operation, the process can include emanating a radioactive gas generated from a source isotope within a source material to separate the radioactive gas as a pure product. Then, the separated radioactive gas can be collected and retained for a time sufficient to decay the radioactive gas to yield one or more high purity radioactive daughter isotopes. For example, Ra-224 isotopes from a legacy source can be utilized by introducing the Ra-224 isotopes into the emanation source which can then be mounted into a housing or other device framework to form the radon (e.g., Rn-220) emanation generator. Then, Rn-220 generated by the Ra-224 source material is emanated from the emanation generator separating the gaseous Rn-220 from the Ra-224 isotopes in the emanation source providing a single gas-phase Rn-220 isotope in the generator. Rn-220 gas separated from the emanation generator is then captured in a collection system or device where the gas is retained while the captured gas decays to form non-gaseous daughter isotopes Pb-212 and/or Bi-212 that accumulate in the collection device and can be recovered from the collection device in a pure state for use as radiotherapy isotopes. However, embodiments of the disclosure are not intended to be limited. For example, source isotopes with any decay chain that passes through (Rn) gas that forms (Rn) daughters can be purified as described herein. Exemplary source isotope systems include Thorium-228 and/or Radium-224; Thorium-227 and/or Radium-223; or Thorium-230 and/or Radium-226. Radioactive gases can include Radon-220; Radon-219; and Radon-222. Gaseous isotopes that decay through other noble gas elements such as xenon and krypton may also be utilized. Exemplary radioactive daughter isotopes include Pb-212 and/or Bi-212; Lead-211 and/or Bismuth-211; and Lead-214 and/or Bismuth-214 and daughter isotopes thereof. The collecting step can include cooling the emanated radioactive gas with a cooling device or cryogen to condense or deposit the emanated radioactive gas. The collecting step can also include extracting the radioactive gas on a thin film or a packed column comprised of a soluble salt; or in a thin film or thin film coating comprised of a lipophilic material on a solid support. Then, recovering the radioactive daughter isotopes can be performed utilizing a fluid such as a biologically-compatible aqueous solution. This system and approach can also eliminate need for complex aqueous radiochemical processes including, for example, precipitation, solvent extraction, and column separations utilized in the prior art requiring intense thermal heating to separate, distill, and recover product isotopes. For example, isotope production generators in the prior art do not separate (Rn) generated by the source isotope but allow radon to decay in fluid-filled static columns which are known to have breakthrough problems by containing high-level isotopes in these separation columns. Isotope production and purification of the instant disclosure utilizes separation of radon gas from the source isotope thus reducing need for labor-intensive steps utilized in the prior art to generate production isotopes.

The purpose of the foregoing abstract is to enable the United States Patent and Trademark Office and the public generally, especially the scientists, engineers, and practitioners in the art who are not familiar with patent or legal terms or phraseology, to quickly determine the nature and essence of the technical disclosure of the application. The abstract is neither intended to define the invention of the application which is measured by the claims nor is it intended to be limiting as to the scope of the invention in any way. Various advantages and novel features of the present invention are described herein and will become further readily apparent to those skilled in this art from the following detailed description. In the preceding and following descriptions preferred embodiments of the invention contemplated for carrying out the invention will be shown. As will be realized, the invention is capable of modification in various respects without departing from the invention. Accordingly, the drawings and description of the preferred embodiments set forth hereafter are to be regarded as illustrative in nature, and not as restrictive. The present invention covers all modifications, alternative constructions, and equivalents falling within the spirit and scope of the invention as defined in the claims. Therefore the description should be seen as illustrative and not limiting.

BRIEF DESCRIPTION OF THE DRAWINGS

FIGS. 1A-1B illustrate one embodiment of a radon emanation system and process for production of high purity therapeutic isotopes.

FIGS. 2A-2F show different emanation generators and methods for preparing same.

DETAILED DESCRIPTION

Figure 2A:
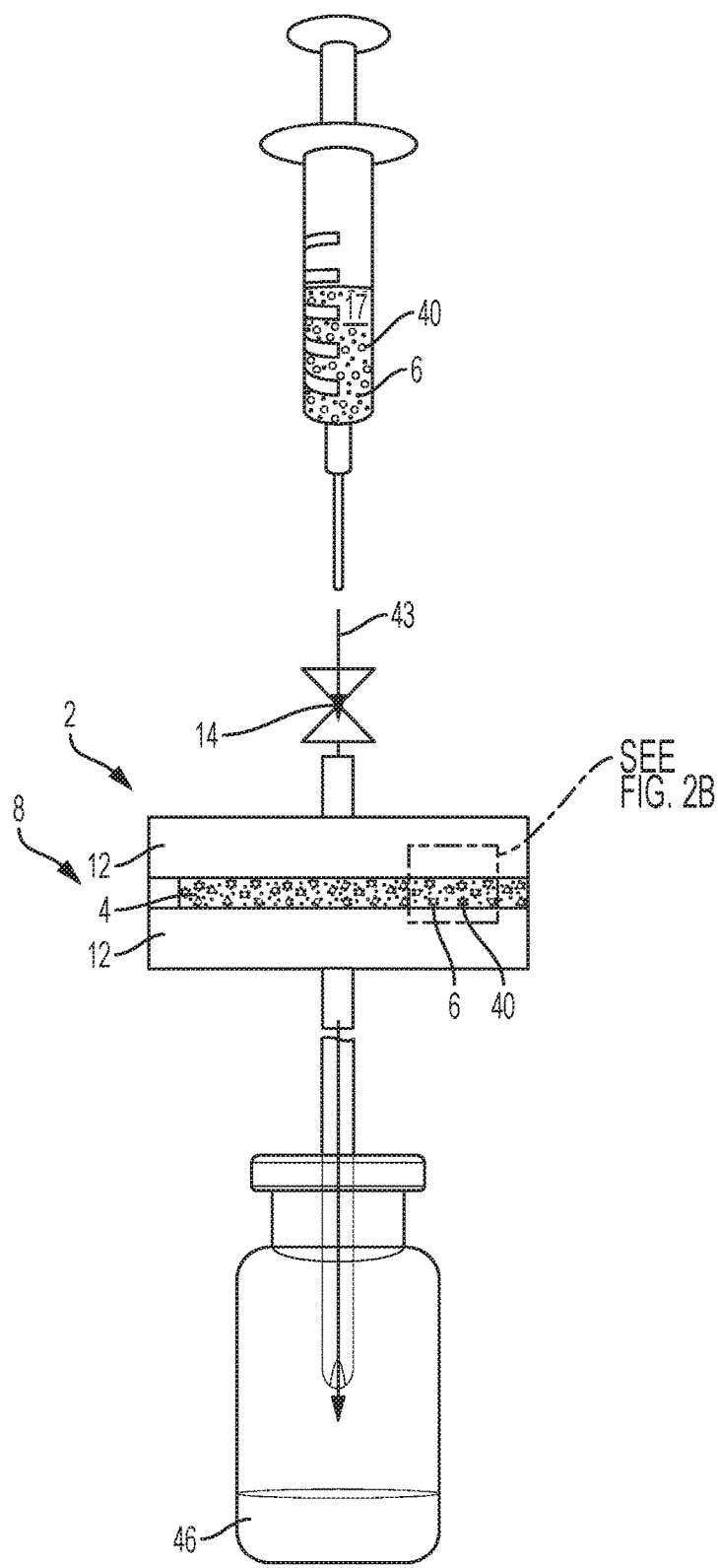

A production system and process are disclosed for producing high purity isotopes for therapeutic applications that address well-known problems in prior art isotope generators including eliminating breakthrough by high energy isotopes that contaminate the recovered product. In the following description, embodiments of the present invention are shown and described by way of illustration of embodiments contemplated and various implementations of embodiments of the disclosure. It will be clear from this description that the invention is not limited to these illustrated embodiments but that the invention also includes a variety of modifications and alternative constructions and embodiments thereof. It will be clear from the following description that the invention is susceptible of various modifications and alternative constructions. While the invention is susceptible of various modifications and alternative constructions, it should be understood that there is no intention to limit the invention to the specific forms disclosed, but, on the contrary, the invention is intended to cover all modifications, alternative constructions, and equivalents falling within the spirit and scope of the invention as defined in the claims. Therefore the description should be seen as illustrative and not limiting.

FIGS. 1-5 show different embodiments of a system and processes for production of high purity isotopes and results demonstrating their effectiveness. The disclosure is not intended to be limited to any specific isotope as the system and processes can be configured for production of other high purity isotopes detailed further herein. Referring first to FIG. 1A, one embodiment of an exemplary isotope production system 100 for production of high purity isotopes 26 for therapeutic applications is shown such as, for example, Pb-212 and/or Bi-212. System 100 includes an emanation generator 2 that includes an emanation source 4 loaded with a source isotope 6. Emanation generator 2 is configured to automatically separate radon generated in the emanation source 4 from other isotopes therein by releasing radon gas 10 as a pure gas or in a carrier gas which generators in the prior art do not do thus enabling various isotope sources to be utilized in the emanation source 4 including, for example, less purified source isotope mixtures 6 and even lower-grade sources which reduces expense and simplifies production of recovered high purity isotopes 26 therein. In one exemplary embodiment, emanation generator 2 can include an emanation source 4 loaded with, for example, a source isotope 6 configured to generate Rn-220 gas 10, for example. Exemplary sources include, for example, a single isotope as well as combinations of isotopes. In some embodiments, the source isotope is a single Ra-224. In other embodiments, source isotopes 6 including long-lived radioisotopes and combinations of these isotopes may also be utilized including, for example, Th-228 and/or U-232, that in prior art generators are problematic. For example, emanation generator 2 is preferably constructed of non-lipophilic materials such as stainless steel that are not subject to radiolytic breakdown as in the prior art so as to not be affected by the emanation gas 10 transported from emanation source 4. These materials are radiolytically stable in prolonged contact with alpha (α) and beta (β) particles emitted by the source isotope 6 therein and enabling the radon (Rn) gas to be generated and delivered at a sustainable and high Rn emanation power which addresses another known problem in prior art generators that utilize lipophilic materials to contain the source isotope which can reduce emanation power in these prior art generators. However, even if radiolytically susceptible source materials 4 are utilized, these emanation source materials can be exchanged before radiolytic breakdown can even take place. Emanation source 4 also does not require high-purity source isotopes to be utilized as in prior art generators that generally require high-purity and single source isotopes to be utilized with the generally involved separation and purification of these source isotopes.

In some embodiments, emanation source 4 containing source isotopes 6 can be arranged, for example, as a column or stack of isotope-bearing membranes, screens, filters, and porous discs that enables a greater quantity of the source isotope 6 or a more dispersed source isotope 6 to be assembled within a fixed diameter or geometry in emanation generator 2 to provide a maximum emanation power for generating the emanation gas 10.

In the exemplary embodiment, radon emanation generator 2 containing the installed Ra-224 (and Rn-220 producing) emanation source 4 provides efficient emanation and delivery of the Rn-220 emanation gas 10 at a high Rn-220 emanation power. Emanation power (E) for Rn-220, for example, is given by the ratio of the activity of the Rn-220 and any of its resulting daughter isotopes collected in the collection stage 24 to the activity of the Ra-224 source isotope 6 in the emanation source 4. An emanation power greater than or equal to about 60% is preferred and more preferably greater than or equal to about 90%.

System 100 has a modular design in which emanation source 4 containing the source isotope (generation nuclide) 6 is positioned, for example, within a housing 8 or other assembly whereby the emanation generator 2 can be readily decoupled from the collection device 24 enabling the emanation generator 2 and/or source isotope 6 to be replaced or exchanged with a same or different emanation generator 2 and/or source isotope 6 due to the finite lifetime of isotope source 6 due to radioactive decay. Exchange or replacement of isotope source 6 or emanation generator 2 enables emanation source 4 to provide a maximum radon emanation power without reduced production of resulting high-purity product isotopes. Modularity of emanation generator 2 and emanation source 4 addresses well-known problems of radiolytic breakthrough in prior art generators by enabling exchange of the emanation device 2 and/or emanation source 4.

In one exemplary embodiment, housing 8 can comprise two metal disks 12 constructed of corrosion-resistant stainless steel, for example. A valve 14 coupled to housing 8 can be utilized to introduce a carrier gas 1 through emanation source 4, and emanation generator 2, for example. An outlet valve 16 can be utilized to deliver separated emanation gas 10 out of emanation source 4 and away from emanation generator 2, for example. In some embodiments, several emanation devices 2 and collection devices 24 can run in tandem or parallel to maximize process efficiency utilizing respective eluent delivery systems 36 to provide optimal recovery of product isotopes 26 for maximum collection yields. In some embodiments, an eluent delivery system 36 such as a switchable valve system can be utilized to deliver a single eluent 37 to the collection device 24 to maximize efficiency of isotope recovery of radon decay products 26. In other embodiments, the eluent delivery system 36 can include a digital syringe pump or other fluid dispensing devices, for example, with output lines connected to inlet valve 16 that deliver eluents 37 into the collection assembly 24 for recovery of product isotopes 26, for example. The trap 24 outlet 18 can be connected to various collection systems 26 and devices 26 including fraction collectors and septa vials, for example. Eluent delivery system 36 can deliver various eluent solutions 37 and volumes at various flow rates, for example. Elution profiles of the Pb-212 can be determined and charted, for example, by counting each collected elution fraction with a gamma detector. Various computer-controlled devices can be utilized to automate components or devices within system 100 to automate any suitable aspect of isotope production and to provide consistent production results in each production cycle. Automation also enables higher-activity sources behind shielding to be utilized thereby minimizing radiologic handling doses. System 100 can also include a scrubber system 22 configured, for example, to remove any non-collected radon-derived isotopes that might reside, for example, in the carrier gas 1 before releasing carrier gas 1 from the system 100 or recycling the carrier gas 1 for reuse. Activated charcoal or similar materials installed in a scrubber 22 provide high scrubbing efficiency for radon, for example.

System 100 can also include a collection device or system 24 that captures emanation gas 10 released from emanation generator 2. The emanated Rn-220 gas 10 undergoes radioactive decay in the collection system 24 for a time sufficient to form pure Pb-212 and/or Bi-212 product isotopes 26 (see FIG. 1B) that accumulate in a pure state therein. After collection, these isotopes can be eluted from the collection system 24, for example, with a biologically-compatible aqueous solution such as physiological saline or other pH neutral eluent solutions, for example, that are compatible with proteins utilized for isotope labeling, for example. These eluent solutions 37 enable product isotopes 26 to be recovered and directly utilized for therapeutic treatment and/or diagnostic imaging, for example. Other biologically-compatible eluent solutions may be utilized including, for example, isotonic solutions, buffered solutions such as acetate buffers; carbonate/HEPES buffer solutions; urea solutions; and combinations of these various solutions. Biologically-compatible eluents can eliminate need for high concentration acidic solutions such as hydrochloric or other acids and other involved wet chemistry and process steps that in the prior art are required to convert chemical matrices of recovered isotopes. For example, prior art systems and approaches generally require acidic solutions as eluents to recover product isotopes and thereafter heating to remove these unsuitable chemical matrices by evaporation with re-dissolution of dried residual salts in an appropriate labeling solution. Alternatively, prior art systems require addition of buffering agents to the eluted isotope products to bring pH to an appropriate level for labeling. Each step adds time, labor, and materials costs to processing. These biologically-compatible solutions enable quantitative elution and recovery of the Pb-212 and/or Bi-212 product isotopes 26 from collection system 24 with minimal to no processing after recovery. For example, as shown in FIG. 1B, eluents 37 can be introduced into the capture device 24, for example, by opening an inlet valve 16 leading into the capture device 24 enabling the eluent 37 to flow through the capture device 24 to recover product isotopes 26 formed therein. Eluted product isotopes can be recovered, for example, by opening an outlet valve 18 positioned, for example, at the releasing end of the collection device 24 enabling eluted product isotopes 26 to be recovered (e.g., periodically) from the collection system 24 for intended therapeutic applications, for example. Various valves and valve systems or tees can be utilized for introducing carrier gases and eluents into and out of various devices and/or processing stages within system 100 at various processing points. As such, number and position of valves and valving systems and tees are not intended to be limited.

Figure 2B:
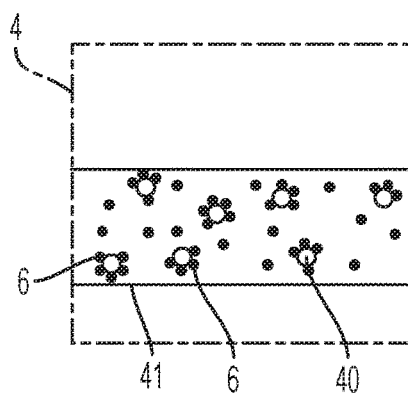

In one exemplary approach for preparing emanation source 4 shown in FIG. 2A and FIG. 2B, a quantity of solid sorbent particles 40 containing source isotopes or generator nuclides 6 adsorbed on the surfaces of sorbent particles 40 can be introduced through an inlet valve 14 as a suspension 43 suspended in a carrier fluid 17 or source 6 liquid 17 and collected with a permeable support 41 such as by sorption or deposition with a filter 41 that forms emanation source 4. Filtrate 46 can be recovered. Other methods can also be utilized as described further herein.

Figures 2C, 2D:
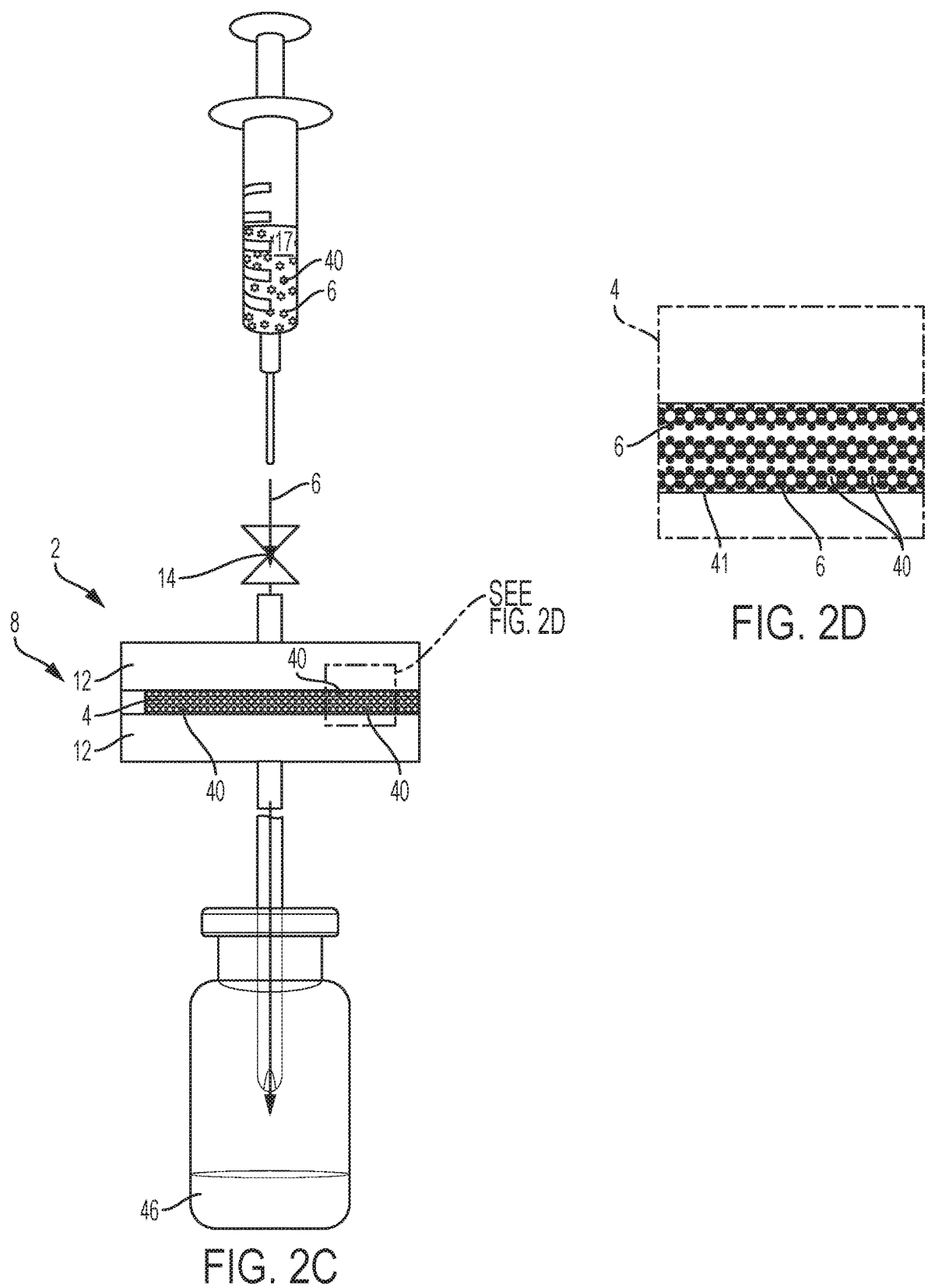

In another exemplary approach shown in FIG. 2C and FIG. 2D, a solution 17 containing the source isotope 6 can be delivered, for example, through the inlet valve 14 in emanation generator 2 and collected such as by sorption or deposition on surfaces of sorbent particles 40 that are supported on a preassembled membrane 41 such as a permeable metal membrane, screen, or filter that forms emanation source 4. Filtrate liquid 46 can be recovered. In some embodiments, sorbent particles 40 can be high surface area metal oxide particles such as iron magnetite (Fe3O4) particles or other particles with chemistries that provide a high adsorption coefficient for preferential collection and retention of source isotopes 6 on surfaces of these particles 40 in emanation source 4. Particles 40 can be magnetic or paramagnetic or even chemically-modified magnetic or paramagnetic particles 40.

In another exemplary approach shown in FIG. 2E and FIG. 2F, a carrier liquid 17 containing sorbent particles 40 such as magnetic or paramagnetic nanoparticles 40 with source isotopes 6 sorbed thereon can be delivered, for example, as a particle 40 suspension 43 through inlet valve 14 for collection on a porous metal support 41 such as a metal frit or metal filter or a metal screen filter while applying a magnetic field to the metal support 41 utilizing a magnet 44, for example, to collect the metal particles 40 on the surface of the metal support 41 while allowing filtrate liquid 46 to pass through the metal support 41 for collection. Then, the filter 41 containing the captured particles 40 can be dried to form the emanation source 4 introduced into the emanation generator 2 prior to operation. Other approaches can also be envisioned such as evacuating the carrier liquid 17 and transferring the particles, or by, for example, removing the magnetically aggregated particles 40 from the source 6 liquid by evacuation through a directly coupled metal support 41 coupled to an evacuation line. Other collection methods are also envisioned. For example, system 100 can be easily configured for loading source isotopes 6 into emanation source 4 through inlet valve 14 as described, for example, and then configuring the system 100 for capture of Rn gas 10 as described herein.

In another exemplary approach, the source isotope 6 can be deposited onto an emanation source 4 by deposition methods such as electrodeposition, for example. A gas-permeable filter, screen, or porous disc 41 may be utilized having suitable conducting properties that enable functioning as an electrode when placed in the electrodeposition chamber. Then, when immersed in an appropriate electrolyte solution containing the source isotope 6 at an appropriate voltage potential or current condition, the source isotope 6 can be electrolytically deposited onto the surface of the gas-permeable filter, screen, or porous disc 41. Upon removal from the electrolyte solution depleted of source isotope 6, the gas-permeable filter, screen, or porous disc 41 now loaded with the source isotope 6 can form an emanation source 4 that can be utilized in an emanation generator 2.

Figure 3B:
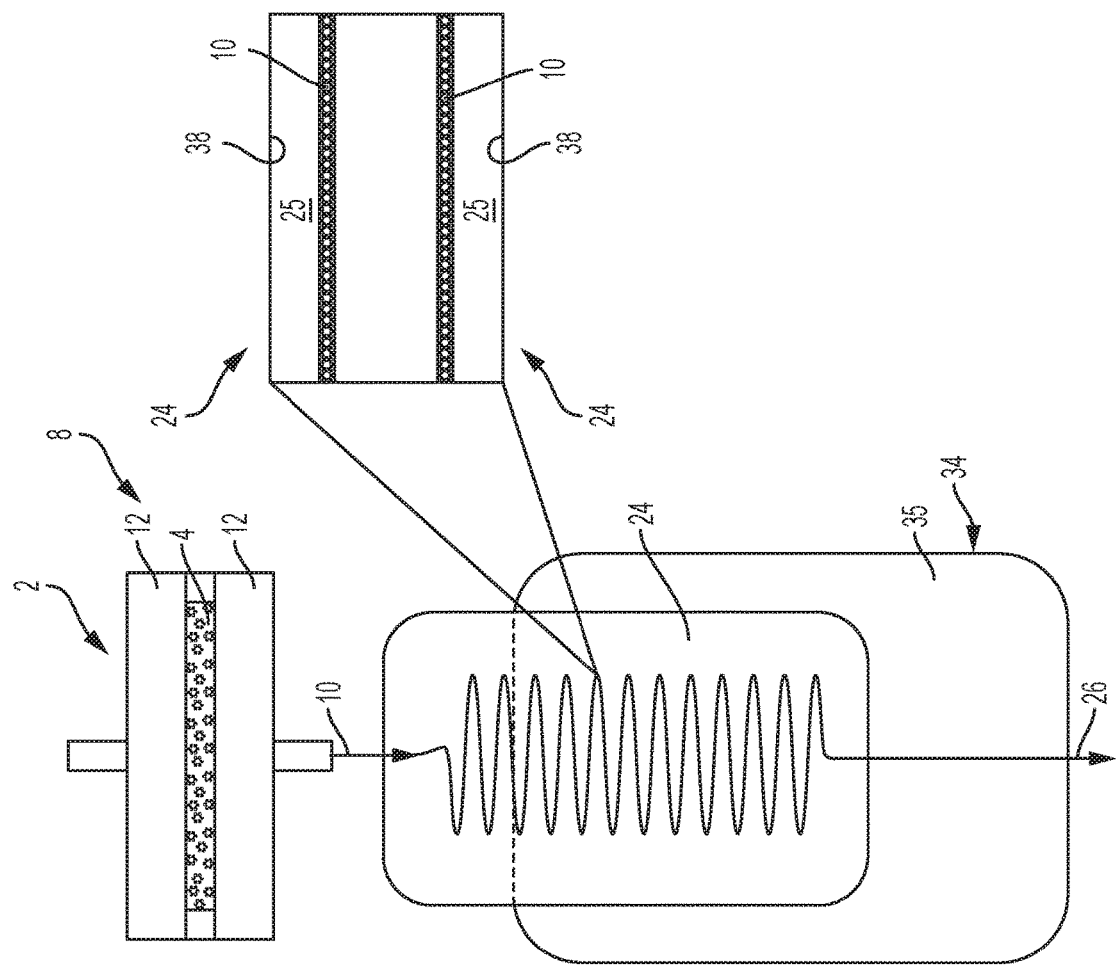
FIGS. 3A-3C show exemplary gas capture and collection devices.
Figure 3A:
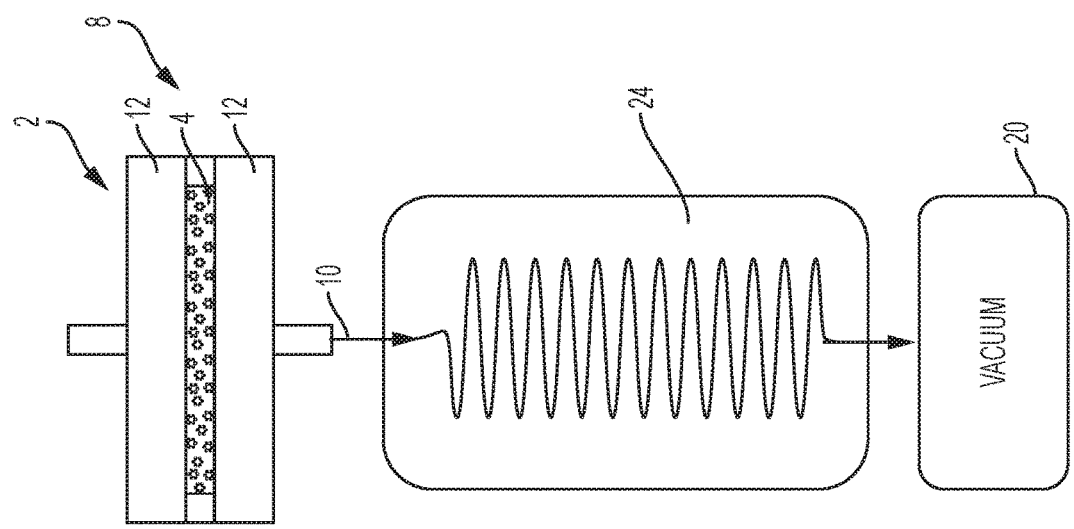
Figure 3C:
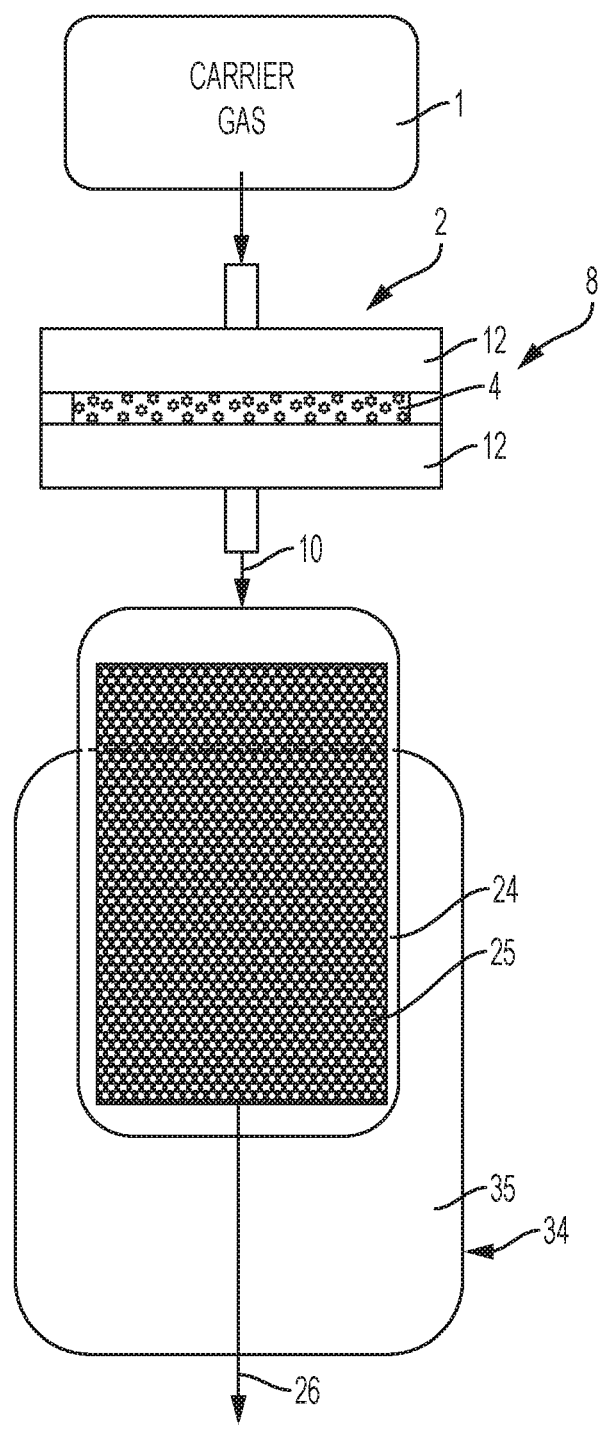

In some embodiments, gas collection system 24 can be coupled to a vacuum device 20 as shown in FIG. 3A that is configured to pull the emanation gas 10 released from the emanation generator 2 into the collection device 24 for capture of the emanation gas therein. In the instant embodiment, collection device 24 can include a tube 24 constructed of a suitable material such as corrosion resistant stainless steel, for example, with a convoluted or serpentine shape to increase the surface area for collection of the emanation gas 10 therein. Tube 24 has a sufficient length, for example, to retain captured radon gas 10 and allow decay into the Pb-212 and/or Bi-212 isotope daughter products therein which can be recovered as described above.

In another embodiment shown in FIG. 3B, collection device 24 can include a capture material 25 such as a sorbent introduced, for example, as a thin film 25 onto an inner wall 38 that captures radon gas 10 by extraction, sorption, or deposition when transported from emanation generator 2. The capture material 25 may be include soluble inorganic salts such as buffer salts and physiological salts; organic salts such as urea; and soluble organic proteins such as gelatins that extract the emanation gas 10 in the thin film 25, as shown. In some embodiments, the thin film capture material 25 can be comprised of lipophilic materials including long-chain hydrocarbons such as dodecane, for example.

Collection device 24 can also be cooled with cooling devices 34 as shown such as thermoelectric cooling devices (e.g., Peltier devices); chilled fluid delivery devices; Dewar devices filled with liquid cryogens such as liquid nitrogen or dry ice bath; gas traps; and cooled adsorption devices. As shown in the figure, the collection device 24 is encompassed within the cooling zone 35 to enhance capture of the emanation gas 10 in the collection device 24. These cooling devices enable the emanation gas 10 to condense within the collection device 24 enabling the radon gas 10 to be captured at a temperature at or near the cryogenic temperature, for example. In one example, emanated radon gas 10 can be collected, for example, by cooling the collection tube 24 in a cooling zone 35 filled with liquid nitrogen or a dry ice bath and condensing the gas 10 at a temperature at or near the cryogenic temperature, for example. In another example, the collection device 24 can be immersed into a Dewar type cooling vessel 34 containing a liquid cryogen as cooling zone 35 enabling radon gas 10 introduced through the collection tube 24 to be condensed or deposited and captured therein. Decay of the captured emanation gas 10 can then be allowed to take place to form the daughter products 26 as described previously above. In another embodiment shown in FIG. 3C, collection device 24 can also be filled or packed with the radon capture sorbent 25 such as with the soluble inorganic or organic capture salt to completely capture the emanation gas 10 in collection device 24. In some embodiments, the thin film capture material 25 can be comprised of lipophilic materials coated on a solid support such as a metal or resin bead.

Collection device 24 can also be coupled to a cryogenic cooling device 34 or cryogen 34, for example, to encompass the cooling device and capture material 25 in a cooling zone 35 to enhance capture of the emanation gas 10 in the collection device 24. Cooled surfaces 38 and/or capture materials 25 within the collection device 24 can be warmed, for example, to a temperature such as room temperature to facilitate collection of accumulated product isotopes 26 such as Pb-212 and/or Bi-212 daughter 26 at a high purity via elution. Collection of the daughter isotopes 26 can be performed, for example, by removing the collection device 34 from the cooling zone 35 to warm the collection device 24 and/or the capture material 25 enabling collection of the product isotopes 26 utilizing an eluent 37 delivered from an eluent delivery system 36, for example.

Upon introduction of the eluent solution 37 into the collection tubing 24 or packed column 24, the soluble capture salt or protein 25 that retains the product isotopes becomes soluble in the eluent solution 37 which dissolves the capture salt or packed salt 25 to release the retained product isotopes into solution enabling recovery of the product isotopes 26 in the eluent solution 37. Alternatively, the eluent solution 37 can act in a solvent extraction process to remove isotope products 26 from lipophilic thin films 25 or lipophilic coatings 25 on metal or resin beads, for example.

Various combinations of these different configurations and embodiments can also be utilized. Purity of the eluted isotope products 26 is high with chemical yields preferably greater than or equal to about 60% and more particularly greater than or equal to about 90%.

In preferred embodiments, cooling device 34 can be utilized as a switchable cold source that in cooling mode condenses or deposits the emanation gas 10 onto the capture material 25 enabling capture and collection of the radioactive gas 10 in the cooled collection device 24. In addition, switching between cooling and warming modes can be activated remotely, for example, via computer enabling effective capture during the cooling cycle and elution of daughter isotopes 26 during the warming cycle. Various alternative approaches are also envisioned.

Example 1

Figure 4:
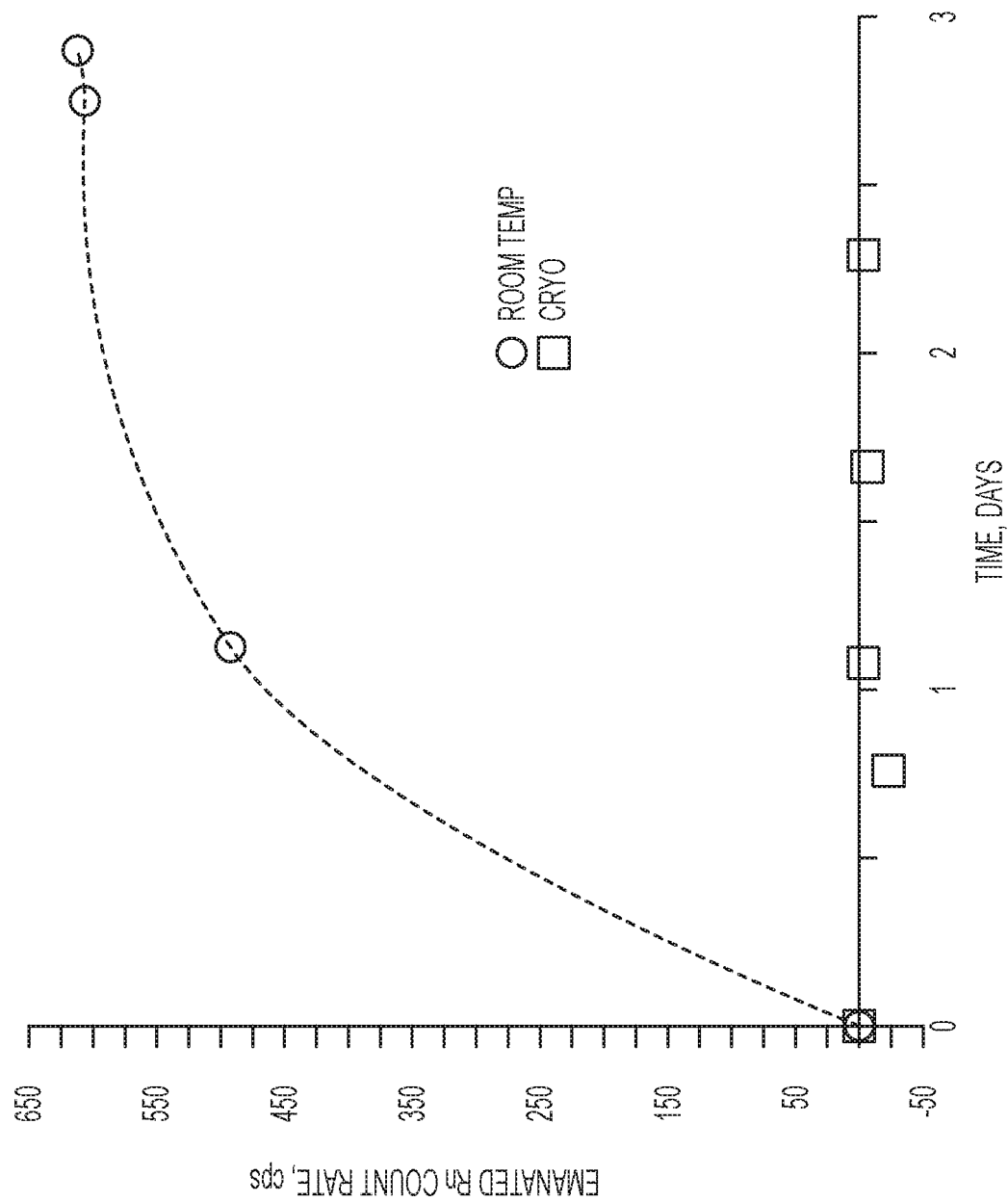
FIGS. 4-5 show different radon collection results.

One embodiment of an isotope production system was utilized. Cryogenic capture of Rn-220 gas via deposition from a carrier gas stream was demonstrated. A gas flow assembly was utilized having a gas emanation source loaded with ~50 kBq Th-228/Ra-224 isotope mixture that was sorbed onto 1 mg of magnetite (Fe3O4) particles that were chemically modified to include MnO2 (e.g., forming Mn-doped Fe3O4). Particles were collected on a gas permeable syringe filter disc forming a radon emanation source that was then coupled atop a coiled stainless steel tube. The tube outlet was connected to a scrubber filled with activated charcoal to collect and provide quantitative capture of any Rn-220 gas released through the coiled tube. The coiled tube was configured to be immersible into a 1 L Dewar filled with liquid nitrogen while the activated charcoal scrubber remained positioned outside the cooling zone. FIG. 4 presents radiological counting (activity) results for Rn-220 gas in the activated charcoal trap both with and without cryogenic cooling. At room temperature, capture results show that Rn-220 gas was delivered through the coiled tube and captured in the activated charcoal trap. Cryogenic cooling results show Rn-220 gas from the emanated gas stream was quantitatively deposited and captured in the coiled stainless steel tube; no Rn-220 was delivered to the activated charcoal trap.

Example 2

Figure 5:
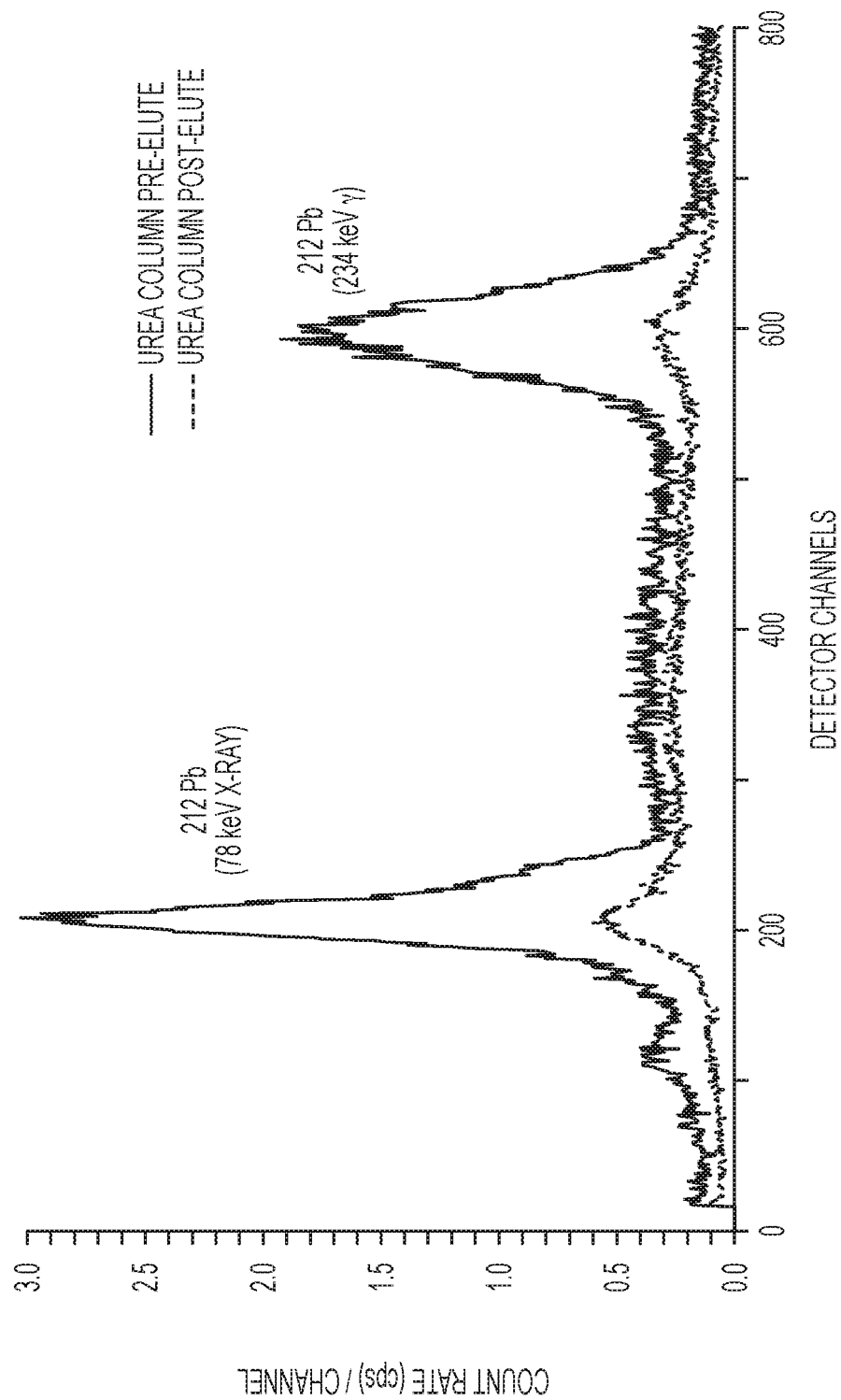

The emanation source of Example 1 was utilized. Rn-220 gas was captured onto a column packed with a soluble salt comprised of solid urea powder utilizing a phase change induced by cryogenic cooling and physisorption. The column packed with urea powder was connected between the emanation source and a scrubber containing activated charcoal therein. The packed column was immersed in a Dewar containing liquid nitrogen and carrier gas was then delivered through the system. The collection column was removed from the cryogen after ~2 days and Pb-212 product isotopes resulting from Rn-220 decay were detected with a gamma detector to establish activity on the column. 5 mL of physiological saline were then delivered through the column to dissolve the urea powder to recover the Pb-212 product isotopes captured therein. Residual activity within the column after urea salt was removed was again measured by the gamma detector. FIG. 5 shows the Pb-212 activity before and after elution of the column with physiological saline. Preliminary results showed that ~87% of the Pb-212 originally in the column was recovered from the column when the urea capture salt was dissolved by physiological saline. Further optimization is expected to increase recovery.

While a number of embodiments of the present invention have been shown and described, it will be apparent to those skilled in the art that many changes and modifications may be made without departing from the invention in its broader aspects. The appended claims are therefore intended to cover all such changes and modifications as fall within the scope of the invention.

What is claimed is:

1. A method of producing radioisotopes, the method comprising:
    preparing a composition comprising an Ra source isotope and sorbent particles;
    loading the composition onto a solid support material to form a mixture comprising the Ra source isotope, the sorbent particles, and the solid sorbent material;
    while within the mixture, decaying at least some of the Ra source isotope to yield one or more radioactive Rn daughter isotopes in a gaseous state;
    separating the gaseous Rn daughter isotopes from the mixture; and
    collecting the separated Rn daughter isotopes.

2. The method of claim 1 wherein the source isotope comprises one or more of Radium-224, Radium-223, and/or Radium-226.

3. The method of claim 1 wherein the radioactive gas comprises one or more of Radon-220, Radon-219, and/or Radon-222.

4. The method of claim 1 further comprising forming decay products of the collected Rn daughter isotopes.

5. The method of claim 4 wherein the decay products comprise one or more of Pb-212, Bi-212; Pb-211, Bi-211, Pb-214, and/or Bi-214.

6. The method of claim 1 wherein the sorbent particles comprise magnetic and/or paramagnetic metal oxide particles.

7. The method of claim 1 wherein the solid sorbent material is gas-permeable.

8. The method of claim 1 wherein the collecting the separated Rn daughter isotopes further comprises cooling the daughter isotopes.

9. The method of claim 1 wherein the collecting the separated Rn daughter isotopes further comprises binding the daughter isotopes to a support having an affinity for the daughter isotope in gaseous form.

10. The method of claim 9 wherein the support comprises a soluble salt configured as a thin film or a packed salt.

11. The method of claim 9 wherein the support comprises a lipophilic liquid configured as a thin film.

12. The method of claim 9 wherein the support comprises a thin film coating on a solid support.

13. The method of claim 1 wherein the collecting the separated Rn daughter isotopes comprises collecting the daughter isotopes in a liquid solution.

* * * * *